United States Patent [19]

Bhalay

[11] Patent Number: 6,114,468
[45] Date of Patent: Sep. 5, 2000

[54] SYNTHETIC RESINS FOR USE IN SOLID PHASE SYNTHESIS

[75] Inventor: Gurdip Bhalay, Horsham, United Kingdom

[73] Assignee: Novartis AG, Basel, Switzerland

[21] Appl. No.: 09/088,500

[22] Filed: Jun. 1, 1998

[51] Int. Cl.[7] .................................................. C08F 8/30
[52] U.S. Cl. ................................. 525/333.3; 525/332.2; 525/333.5; 525/333.6; 525/352
[58] Field of Search ............................. 525/333.3, 333.5, 525/333.6, 332.2, 352

[56] References Cited

U.S. PATENT DOCUMENTS

| | | | |
|---|---|---|---|
| 4,038,469 | 7/1977 | Walker et al. | 526/19 |
| 4,076,913 | 2/1978 | Walker et al. | 526/19 |
| 5,004,781 | 4/1991 | Rink | 525/54.11 |
| 5,324,833 | 6/1994 | Sieber et al. | 544/183 |

OTHER PUBLICATIONS

Chapman et al., "Amino Acids and Peptides. Preparation and Reactions of a Polymer Diazomethylene," J.C.S. Chem. Comm., 1975, pp. 690–691.

Dudman, C. C. et al., "Preparation of Aryldiazoalkanes from 2,4,6–Triisopropylbenzenesulphonyl Hydrazones," Synthesis, 1982, pp. 419–421.

Lu, Gui–shen et al., "Improved Synthesis of 4–Alkoxybenzyl Alcohol Resin," J. Org. Chem., vol. 46, 1981, pp. 3433–3436.

Wang, Su–Sun, "p–Alkoxybenzyl Alcohol Resin and p–Alkoxybenzyloxycarbonylhydrazide Resin for Solid Phase Synthesis of Protected Peptide Fragments," J. Am. Chem. Soc., vol. 95, 1973, pp. 1328–1333.

*Primary Examiner*—Bernard Lipman
*Attorney, Agent, or Firm*—David E. Wildman; Stephen G. Kalinchak

[57] ABSTRACT

A polystyrene resin which is substituted in skeletal benzene rings thereof by a group of formula

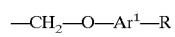

I where $Ar^1$ is an unsubstituted or substituted phenylene group and R is a group of formula

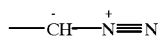

II or a precursor group for a group of formula II, said precursor group being of formula

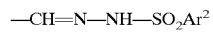

III where $Ar^2$ is an aryl group.

11 Claims, No Drawings

SYNTHETIC RESINS FOR USE IN SOLID PHASE SYNTHESIS

This invention relates to synthetic resins, in particular polystyrene resins, which are suitable for use as supports in solid phase chemical synthesis, the preparation of such resins and their use in chemical synthesis.

Polystyrene resins have repeating units of formula

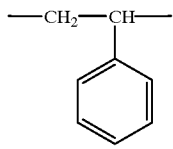

in which the indicated benzene rings, the skeletal benzene rings, may be unsubstituted as shown above or may be substituted by property-modifying groups, or some of the skeletal benzene rings may be unsubstituted and some of them substituted by such groups.

Polystyrene resins for use as supports in solid phase chemical synthesis are commercially available. These resins have at least some of the skeletal benzene rings substituted by groups which facilitate the attachment of reactants, particularly those containing carboxyl groups, to the resins. For example, commercially available resins include those in which skeletal rings are substituted by a group of formula —$CH_2$—O—Ph—$CH_2$OH where Ph is a p-phenylene group. Conventional procedures for the attachment of carboxylic acids to such resins, for example in peptide synthesis, inherently introduce the possibility of racemisation of an alpha-stereogenic centre; furthermore these procedures involve the use of stringent conditions and the wasteful use of a large excess of the carboxylic acid.

It has now been found that polystyrene resins having certain novel substituents exhibit highly desirable properties. In particular, they facilitate attachment of carboxylic acid reactants by a rapid colourmetric reaction under relatively mild conditions, which reaction does not require the use of a large excess of carboxylic acid, does not compromise the integrity of an alpha-stereogenic centre and permits the attachment of carboxylic acid reactants having amino or hydroxy groups which do not have to be protected as in conventional solid phase synthetic procedures.

Accordingly, the present invention provides, in one aspect, a polystyrene resin substituted in skeletal benzene rings thereof by a group of formula —$CH_2$—O—$Ar^1$—R    I where $Ar^1$ is an unsubstituted or substituted phenylene group and R is a group of formula

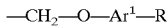    II or a precursor group for the group of formula II, said precursor group being of formula —CH=N—NH—$SO_2Ar^2$    III where $Ar^2$ is an aryl group.

The resin is preferably in crosslinked, but solvent-swellable form, particularly crosslinked by up to 5 mol %, especially 1 to 2 mol %, of divinylbenzene, which is usually incorporated into the resin by copolymerisation with unsubstituted and/or substituted styrene monomers.

In formula I, $Ar^1$ may be phenylene which is unsubstituted or substituted by one or more, preferably one or two, $C_1$ to $C_4$ alkyl groups, which may be methyl, ethyl, n-propyl, isopropyl, n-butyl, sec-butyl, isobutyl or tert-butyl, or $C_1$ to $C_4$ alkoxy groups, which may be methoxy, ethoxy, n-propoxy, isopropxy or butoxy, preferably methoxy. Preferably $Ar^1$ is unsubstituted phenylene.

$Ar^2$ in formula III may be a $C_6$ to $C_{10}$ aryl group, usually a phenyl group which is unsubstituted or substituted by one or more alkyl groups, preferably by one or more, especially two or three, branched alkyl groups preferably having 3 to 6 carbons, more especially 3 or 4 carbon atoms. In a particularly preferred embodiment, $Ar^2$ is phenyl substituted by three isopropyl groups, most preferably 2,4,6-tri-isopropylphenyl.

Resins of the invention where R is a group of formula II may be prepared by reacting a resin of the invention where R is a group of formula III as hereinbefore described with an alkali, preferably potassium hydroxide, in an alcohol solvent or a mixture thereof with an ether solvent, preferably a mixture of methanol and tetrahydrofuran (THF). The reaction may be carried out at 85–95° C., using the protocol of Reese et al, Synthesis 1982, 5, 419–421.

Resins of the invention where R is a group of formula III may be obtained by reacting a polystyrene resin substituted in skeletal benzene rings thereof by a group of formula —$CH_2$—O—$Ar^1$—CHO    IV where $Ar^1$ is as hereinbefore defined, said resin preferably being crosslinked by up to 5 mol % of divinylbenzene, with a sulfonyl hydrazide of formula $H_2N$—NH—$Ar^2$    V where $Ar^2$ is as hereinbefore defined. The reaction may be carried out using known procedures for aldehyde-hydrazide reactions, for example in an organic solvent such as THF at 15–30° C.

Polystyrene resins substituted by groups of formula IV and crosslinked by up to 5 mol % of divinylbenzene, and sulfonyl hydrazides of formula V are commercially available or may be prepared by known procedures.

Resins of the invention substituted by groups of formula I where R is a group of formula II may be used as supports in solid phase chemical synthesis. They are particularly useful as supports in synthetic procedures requiring the attachment of a carboxylic acid to the support, for example solid phase peptide synthetic procedures. Resins of the invention where R is a group of formula II may be reacted with a carboxylic acid of formula $R^1$ COOH to give a resin substituted in skeletal benzene rings thereof by a group of formula —$CH_2$—O—$Ar^1$—$CH_2$—O—$COR^1$    VI where $Ar^1$ is as hereinbefore defined and $R^1$ is the residue of a carboxylic acid of formula $R^1$ COOH after removal of the indicated carboxyl group. The carboxylic acid $R^1$ COOH may be, for example, a hydrocarbyl carboxylic acid such as an alkane-, alkene-, alkyne-arene-, aralkane-, cycloalkane- or benzocycloalkane-carboxylic acid, a hydroxycarboxylic acid such as an arylhydroxyalkyl carboxylic acid, or an aminocarboxylic acid or an amino- and hydroxy- substituted carboxylic acid such as those used in peptide synthesis.

The reaction may be carried out in an organic solvent such as dichloromethane or dimethyl formamide. It is conveniently carried out at ambient temperature. In general, the reaction is accompanied by a distinctive change in colour of the resin, providing a convenient visual means of monitoring the reaction. The reaction proceeds by a mechanism which does not compromise the integrity of an alpha-stereogenic centre.

Accordingly, the present invention also provides a method of carrying out solid phase chemical synthesis which comprises (A) reacting a resin of the invention in which R is a group of formula II with a first reactant to give a resin-bound reactant, (B) reacting the resin-bound reactant with a second reactant to give a resin-bound product, (C) optionally subjecting the resin-bound product to one or more further chemical reactions and (D) detaching the product of step (B) or (C) from the resin by cleavage of a bond formed in step (A), e.g. by acidolysis. The method is particularly useful where the first reactant is a compound containing a carboxyl group which is reactive with the group of formula II and a functional group, such as an amino group or a hydroxy group, which is either not reactive under the conditions used for the reaction of the resin with the first reactant or is in protected form. Suitable amino-protecting groups and hydroxy-protecting groups are well known in the art. In general, however, it has been found that a resin of the invention where R is a group of formula II may be reacted with a hydroxy-substituted carboxylic acid without the need to protect the hydroxy group and may be reacted with an amino-substituted carboxylic acid without the need to use conventional amino-protecting groups and procedures by protonating the amino nitrogen atom of such an acid, for example using a sulfonic acid such as p-toluenesulfonic acid, before reaction with the resin.

Where the first reactant is an aminocarboxylic acid or a hydroxycarboxylic acid, the resin-bound reactant (obtained as a product of the reaction of the resin and the first reactant) may be reacted through an amino group or hydroxy group respectively with the second reactant. Of course, if the amino group or hydroxy group in the resin-bound reactant is in protected form, it should be deprotected when required for reaction with the second reactant. Where the first reactant is an aminocarboxylic acid or hydroxycarboxylic acid, the second reactant may be an aminocarboxylic acid or a hydroxycarboxylic acid or an acylating derivative thereof such as an acid halide, anhydride or reactive ester thereof, the amino group or hydroxy group of the second reactant optionally being in protected form. The reaction between the resin-bound reactant and the second reactant may be carried out using conventional procedures. The resin-bound product of this reaction may, if desired, be subjected to further reactions, for example to successive further reactions with aminocarboxylic or hydroxycarboxylic acids or acylating derivatives thereof. When the first reactant is a carboxylic acid and the desired number of reactions have been carried out, the resin is substituted in skeletal benzene rings thereof by a group of formula —CH$_2$—O—Ar$^1$—CH$_2$—O—COZ   VI where Ar$^1$ is as hereinbefore defined and Z is the residue of the carboxylic acid first reactant as modified by any subsequent reactions. The product of the reaction sequence, represented by HO—COZ, may be detached from the resin by acidolysis, which may be carried out using known acidic reagents and procedures, preferably by treatment with aqueous trifluoroacetic acid at ambient temperature.

It will therefore be apparent that the solid phase synthetic method of the invention is applicable to the synthesis of peptides, in which the first amino acid is reacted through a carboxyl group thereof with the resin of the invention where R is a group of formula II to become attached to the resin and is then reacted successively with one or more further amino acids, for example using conventional procedures, until the desired amino acid sequence is obtained, the resulting peptide then being detached from the resin by acidolysis as hereinbefore described.

In view of the ease with which a group of formula II reacts with a carboxyl group, resins of the invention where R is a group of formula II may be used as scavengers for carboxylic acids.

The invention is illustrated by the following Examples.

EXAMPLE 1

To Aldehyde Wang HL resin, a polystyrene substituted in skeletal benzene rings by a group of formula IV where Ar$^1$ is phenylene and crosslinked by 2 mol % divinylbenzene, available from Novabiochem (4.0 g, 12.96 mmol) is added 2,4,6-triisopropylbenzenesufonyl hydrazide (7.7 g, 25.92 mmol) as a solution in dry THF (40 ml). The suspension is stirred for 16 hours at room temperature, filtered and washed with methanol and dichloromethane (DCM) to give an orange coloured resin bound hydrazone. Dry THF (40 ml) is added and the resin allowed to pre-swell for 10 minutes before the addition of a solution of potassium hydroxide (1.5 g, 25.92 mmol) in dry methanol (10 ml). The mixture is heated at 90° C. for 7 minutes, during which time the resin becomes deep red in colour. The resin is filtered and washed with dry DCM [IR (2050 cm$^{-1}$)].

EXAMPLE 2

To the resin product of Example 1 (300 mg, 0.97 mmol) in DCM (5 ml) at room temperature is added a solution of tetrahydro-α-naphthoic acid (210 mg, 1.20 mmol) in DCM (5 ml). The resin instantly turns yellow and effervesence is observed. After 5 minutes, the resin is filtered and washed with methanol and DCM to give a resin-bound ester (IR 1730 cm$^{-1}$).

EXAMPLES 3 to 7

Using a procedure analogous to that of Example 2, resin-bound esters are prepared from the resin product of Example 1 and the following carboxylic acids:

3

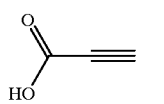

4

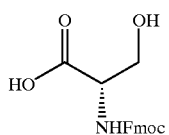

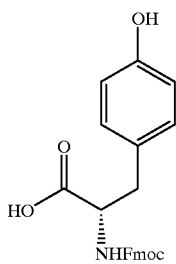

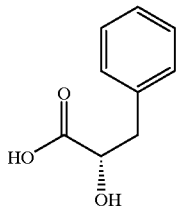

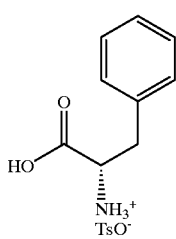

where Fmoc denotes a 9-fluorenylmethoxycarbonyl protecting group and Ts denotes p-toluenesulphonate. The resin-bound esters of Examples 3, 6 and 7 are yellow, while those of Examples 4 and 5 are pink.

EXAMPLES 8 to 13

The resin-bound esters of Examples 2 to 7 are stirred with aqueous 95% trifluoroacetic acid at room temperature for 20 minutes to cleave the respective ester linkages. The resulting mixtures are filtered and the filtrates are evaporated in vacuo to give solids which are confirmed by NMR to be the regenerated carboxylic acids.

What is claimed is:

1. A polystyrene resin which is substituted in skeletal benzene rings thereof by a group of formula —CH$_2$—O—Ar$^1$—R      I where Ar$^1$ is an unsubstituted or substituted phenylene group and R is a group of formula

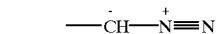      II or a precursor group for a group of formula II, said precursor group being of formula —CH=N—NH—SO$_2$Ar$^2$      III where Ar$^2$ is an aryl group.

2. A resin according to claim 1 which is in crosslinked but solvent swellable form.

3. A resin according to claim 2 which is crosslinked by up to 5 mol % of divinylbenzene.

4. A resin according to claim 3 which is crosslinked by 1 to 2 mol % of divinylbenzene.

5. A resin according to claim 1 in which Ar$^1$ is unsubstituted phenylene.

6. A resin according to claim 5, in which R is a group of formula II.

7. A resin according to claim 1, in which R is a group of formula III, in which Ar$^2$ is phenyl substituted by one or more branched alkyl groups.

8. A resin according to claim 7, in which Ar$^2$ is phenyl substituted by two or three branched C$_3$ or C$_4$ alkyl groups.

9. A resin according to claim 8, in which Ar$^2$ is 2,4,6-triisopropylphenyl.

10. A method of preparing a resin according to claim 1 in which R is a group of formula II wherein the method comprises reacting a resin according to claim 1 in which R is a group of formula III with an alkali.

11. A method of preparing a resin according to claim 1 in which R is a group of formula III wherein the method comprises reacting a polystyrene resin which is substituted in skeletal benzene rings thereof by a group of formula —CH$_2$—O—Ar$^1$—CHO      IV where Ar$^1$ is as defined in claim 1, with a sulfonyl hydrazide of formula H$_2$N—NH—SO$_2$Ar$^2$      V where Ar$^2$ is as defined in claim 1.

* * * * *